United States Patent
Grijpma et al.

(10) Patent No.: US 9,913,932 B2
(45) Date of Patent: Mar. 13, 2018

(54) ARTIFICIAL BONE IMPLANTS, OR BONE GRAFTS, OF POLYMERIC COMPOSITES WITH BONE FORMING PROPERTIES

(75) Inventors: Dirk Wybe Grijpma, Hengelo (NL); Rudolf Robert Maria Bos, Groningen (NL); Anne Cornelis Van Leeuwen, Groningen (NL)

(73) Assignees: UNIVERSITEIT TWENTE, Enschede (NL); RUKSUNIVERSITEIT GRONINGEN, Groningen (NL); ACADEMISCH ZIEKENHUIS GRONINGEN, Groningen (NL)

( * ) Notice: Subject to any disclaimer, the term of this patent is extended or adjusted under 35 U.S.C. 154(b) by 156 days.

(21) Appl. No.: 14/353,486

(22) PCT Filed: Oct. 26, 2011

(86) PCT No.: PCT/EP2011/068718
§ 371 (c)(1),
(2), (4) Date: Jul. 25, 2014

(87) PCT Pub. No.: WO2013/060362
PCT Pub. Date: May 2, 2013

(65) Prior Publication Data
US 2014/0348773 A1    Nov. 27, 2014

(51) Int. Cl.
| | |
|---|---|
| A61L 27/46 | (2006.01) |
| A61L 27/54 | (2006.01) |
| A61L 27/58 | (2006.01) |
| A61L 27/18 | (2006.01) |
| A61L 24/00 | (2006.01) |
| A61L 27/42 | (2006.01) |
| A61L 31/12 | (2006.01) |

(52) U.S. Cl.
CPC .......... *A61L 27/46* (2013.01); *A61L 24/0063* (2013.01); *A61L 27/18* (2013.01); *A61L 27/425* (2013.01); *A61L 27/54* (2013.01); *A61L 27/58* (2013.01); *A61L 31/123* (2013.01); *A61L 2300/112* (2013.01); *A61L 2300/412* (2013.01); *A61L 2300/60* (2013.01); *A61L 2430/02* (2013.01)

(58) Field of Classification Search
None
See application file for complete search history.

(56) References Cited

U.S. PATENT DOCUMENTS 5,679,723 A * 10/1997 Cooper .................... A61L 27/32
                                                              424/426
2005/0208094 A1* 9/2005 Armitage ............... A61K 31/74
                                                              424/423
2006/0008504 A1    1/2006 Kerr et al.
2008/0267901 A1* 10/2008 Grijpma .................. A61L 27/18
                                                              424/78.08
2013/0085563 A1* 4/2013 Stankus ................. A61L 31/041
                                                              623/1.15

FOREIGN PATENT DOCUMENTS

| EP | 0714666 A1 | 6/1996 |
| EP | 1466633 A1 | 10/2004 |
| WO | 2005/027988 A2 | 3/2005 |

OTHER PUBLICATIONS

Zhang et al., "The in vivo and in vitro degradation behavior of polytrimethylene carbonate)" Biomaterials 27: 1741-1748.*
Yang et al., "Biodegradable cross-linked poly(trimethylene carbonate) networks for implant applications: Synthesis and properties", Polymer 54: 2668-2675 (2013).*
Hou et al. "Creep-resistant elastomeric networks prepared by photocrosslinking fumaric acid monoethyl ester-functionalized poly(trimethylene carbonate) oligomers", Acta Biomaterialia 5 (2009), pp. 1543-1551.
Jansen, Janine: "Photo-crosslinked biodegradable polymer networks for controlled intraocular drug delivery", PhD Thesis, University of Twente, Enschede, The Netherlands, Oct. 2011, 172 pages.
Yousefpour et al. "Our Experience in Orbital Floor Reconstruction with a Bioresorbable Polydioxane Implant", Journal of Cranio-Maxillo-Facial Surgery, vol. 24, Aug. 1, 1996, pp. 127.

* cited by examiner

*Primary Examiner* — Robert A Wax
*Assistant Examiner* — Thor Nielsen
(74) *Attorney, Agent, or Firm* — Rudy J. Ng; Bret E. Field; Bozicevic, Field & Francis LLP (57) ABSTRACT

The present invention relates to methods for providing polymeric composites with bone forming, such as with osteogenic and/or osteoinductive and/or osteoconductive, properties. The present invention further relates to polymeric composites provided by the present method and the use of thereof for bone implants, or grafts, specifically the use thereof for orbital floor reconstruction. Specifically, the present invention relates to methods for providing a composite with bone forming properties, the method comprises the steps of: a) providing a liquid, or liquefied, polymeric composition of homopolymers or copolymers of 1,3-trimethylene carbonate (TMC); b) adding to said liquid, or liquefied, polymeric composition one or more agents with osteogenic and/or osteoinductive and/or osteoconductive properties thereby providing a dispersion of said agents in said liquid or liquefied polymeric composition; and c) cross-linking the product obtained, thereby providing a composite with bone forming properties.

16 Claims, 7 Drawing Sheets

ARTIFICIAL BONE IMPLANTS, OR BONE GRAFTS, OF POLYMERIC COMPOSITES WITH BONE FORMING PROPERTIES

The present invention relates to methods for providing polymeric composites with bone forming, such as with osteogenic and/or osteoinductive and/or osteoconductive, properties. The present invention further relates to polymeric composites provided by the present method and the use of thereof for bone implants, or grafts, specifically the use thereof for orbital floor reconstruction.

Ideally bone is regenerated in a treatment of bone defects, or bone fractures, such as orbital floor fractures. The materials currently used, except for autologous bone, for reconstruction of bone, or bone defects, do not regenerate bone and can thus generally be regarded as bone replacement materials.

Bone defects, or bone fractures, are a common result of injury although, especially in the case of bone defects, other causes can be identified such as disease, malnutrition and hereditary disorders. Bone defects, or fractures, are generally treated by reconstruction of the fracture or defect. When reconstructing bony defects, in particular defects of the orbital, herniation of fat and/or entrapment of tissue such as muscle or connective tissue must be avoided as much as possible.

Presently, the use of autologous, or "own derived" bone grafts is considered to be the "golden standard" for repair and reconstruction of bone defects.

However, disadvantages are associated with the use of autologous bone grafts, such as additional surgery, accompanying donor-site morbidity and poor predictability of resorption of the autologous bone.

To avoid these problems, several non-resorbable materials like titanium, polytetrafluoroethylene, polyethylene and silicone rubbers have been applied in the treatment of bone defects, or fractures. However, these materials are not absorbed by the body resulting in a life-long risk of complications.

Also efforts have been directed to the use of biodegradable and bioresorbable implant materials, or grafts, such as polymeric matrices of polylactides and polyglycolides. The use of polylactides and polyglycolides is advantageous as the life-long risk of complications being characteristic for non-resorbable materials can be avoided.

A disadvantage of polylactides and polyglycolides are that their degradation products are known to have negative effects on surrounding tissues and on bone and bone formation. Another disadvantage of the present biodegradable products used for reconstruction of bone defects is excess development of fibrous capsules or scar tissue remaining after degradation of the biodegradable material.

Optimally, bone is regenerated during healing of the bone defect and the regenerated bone becomes connected with the surrounding bone. However, considering the present materials available, this is only, at least partially, the case when autologous bone is used mainly due to its bone forming, such as osteogenic and/or osteoinductive, properties.

Agents having bone forming, such as osteogenic and/or osteoinductive, properties are known and ceramic phosphates, such as calcium phosphates, are promising materials. Several calcium phosphates have been shown to exert bone forming, such as osteoinductive, properties in soft and hard tissues in various animal models. However, the ability to use these ceramic materials as such as bone implants, or bone grafts, remains a problem because of their brittle structures providing, amongst others, insufficient mechanical strength.

Accordingly, there is a need in the art for biodegradable artificial implant materials, or artificial bone grafts, with bone forming, such as osteogenic and/or osteoinductive, properties providing not only bone regeneration but also attachment with, or connection to, the surrounding bone structures. The latter is also designated in the art as osseous integration or osseointegration.

It is an object, amongst other objects, of the present invention to address the above need by providing artificial bone grafts based on biodegradable polymeric matrices, or artificial implant materials, with bone forming, such as osteogenic and/or osteoinductive, properties providing bone regeneration but also attachment with, or connection to, the surrounding bone structures.

The above object, amongst other objects, is met by the present invention as outlined in the appended claims.

Specifically, the above object, amongst other objects, is met, according to a first aspect of the present invention, by methods for providing a composite with bone forming properties, the method comprises the steps of:

a) providing a liquid, or liquefied, polymeric composition of homopolymers or copolymers of 1,3-trimethylene carbonate (TMC);

b) adding to said liquid, or liquefied, polymeric composition one or more agents with osteogenic and osteoinductive properties thereby providing a dispersion of said agents in said liquid or liquefied polymeric composition;

c) crosslinking the product obtained, thereby providing a composite with bone forming properties.

It is noted that laminating the present composite on polymeric layers composed of acidic polymers and/or polymers providing acidic degradation products into a multilayered structure is not part of any method step according to the present invention although laminates of other material or polymers are contemplated within the context of the present invention.

The present inventors have surprisingly discovered that the above methods provide a biodegradable, in another words complete disintegration in time after implantation, composite allowing not only bone formation but also integration of the newly formed bone with the surrounding host bone.

Accordingly, the present bone forming or bone promoting, such as osteogenic and/or osteoinductive, agents embedded in the present polymeric matrix of 1,3-trimethylene carbonate (TMC) (co)polymers are advantageous bone grafts.

According to a preferred embodiment of this first aspect of the present invention, the present one or more agents with bone forming, such as osteogenic and osteoinductive, properties are ceramics selected from the group consisting of calcium phosphates, hydroxyapatite, tricalcium phosphate, octacalcium phosphate, Bioglass, calcium sulphate and biphasic calcium phosphate.

Ceramics such as calcium phosphates, such as hydroxyapatite and tricalcium phosphate, Bioglass and calcium sulphate are biologically active bone formation promoting agent to different degrees largely depending on solubility in the physiological environment. The bone promoting activity of these ceramics can be increased by doping these materials with growth factors, ions such as strontium or mixing with bone marrow aspirate.

According to an especially preferred embodiment, the present ceramic phosphate is biphasic calcium phosphate i.e. a mixture of 20±5% β-tricalcium phosphate (TCP) and 80±5% hydroxyapatite (HA) providing a relatively low solubility in the physiological environment.

β-tricalcium phosphate ($Ca_3(PO_4)_2$) (TCP) is a biocompatible calcium phosphate which occurs naturally in the human body and has a chemical composition that corresponds to the inorganic phase of bone constituting 60% to 70% of human bone. It has been used as a bone filler and bone substitute material. Hydroxyapatite or hydroxylapatite is a naturally occurring mineral form of calcium apatite with the formula $Ca_5(PO_4)_3(OH)$. Up to 50% of bone is made up of a modified form of the inorganic mineral hydroxylapatite.

According to another preferred embodiment of the method according to the present invention, the present dispersion of liquid, or liquefied, polymer and the one or more bone formation promoting agents comprises 5 wt % to 95 wt %, preferably 10 wt % to 90 wt %, more preferably 30 wt % to 70 wt % such as 35 wt %, 40 wt %, 45 wt %, 50 wt %, 55 wt %, 60 wt % or 65 wt %, of the present one or more agents with bone forming, such as osteogenic and/or osteoinductive, properties.

According to yet another preferred embodiment of the method according to the present invention, the present liquefied polymeric composition of homopolymers or copolymers of 1,3-trimethylene carbonate (TMC) has a Mw of more than 50,000 g/mol such as more than 100,000, 150,000, 200,000, 250,000, 300,000, 350,000, 400,000 or 500,000 g/mol.

By providing high molecular weight polymers, i.e. polymers generally comprising more than 500 monomers, in step (a), the physical properties of the resulting composite with bone formation promoting, such as osteogenic and/or osteoinductive, properties according to the present invention can be influenced. High molecular weight polymers will result in an elastomeric material especially suitable to cover relatively large bone defects, such as orbital floor fractures, while providing sufficient support, or mechanical strength, during bone formation.

According to a particularly preferred embodiment of the present method in case high molecular weight polymers are used, the present homopolymers or copolymers are liquefied by dissolution in a solvent, preferably a solvent selected from the group consisting of acetone, dichloromethane, chloroform, carbontetrachloride, ethylene carbonate, propylene carbonate, dimethylsulfoxide, toluene, benzene, tetrahydrofuran or 1,4-dioxane.

Further, according to another particularly preferred embodiment of the present method in case high molecular weight polymers are used, the present method comprises after step (b) but before step (c), a step comprising solidifying, preferably by precipitation or temperatures below the glass transition temperature of the homopolymers or copolymers of 1,3-trimethylene carbonate (TMC), the dispersion and subsequently moulding the solidified dispersion into a desired shape.

Accordingly, the present invention, according to yet another particularly preferred embodiment of the present method in case high molecular weight polymers are used, relates to methods for providing a composite with bone forming or promoting, such as with osteogenic and osteoinductive, properties, comprising the steps of:

a) providing a polymeric composition of homopolymers or copolymers of 1,3-trimethylene carbonate (TMC) with a Mw of more than 50,000;

b) dissolving said polymeric composition thereby providing a dissolved polymeric composition;

c) adding to said dissolved polymeric composition one or more agents with bone forming properties thereby providing a dispersion of said agents in said dissolved polymeric composition;

d) precipitation of said dispersion thereby providing a composite precipitate;

e) moulding said composite precipitate into a desired shape; and f) crosslinking the shaped composite precipitate thereby providing a composite with bone forming properties.

The above crosslinking of step (c), or step (f), of the relatively high molecular weight polymers according to the present invention is preferably provided by gamma radiation with an irradiation dose of 10 to 100 kGy, preferably 10 to 50 kGy, thereby providing an elastomeric composite with bone forming properties.

According to still another preferred embodiment of the method according to the present invention, the present liquid polymeric composition of homopolymers or copolymers of 1,3-trimethylene carbonate (TMC) has a Mw of less than 50,000 g/mol, i.e. polymers generally comprising less than 500 monomers, such as less than 45,000, 40,000, 35,000, 30,000, 25,000 or 20,000 g/mol.

By providing relatively low molecular weight polymers, also designated in the art as oligomers, in step (a), the physical properties of the composite with bone forming, such as osteogenic and/or osteoinductive, properties according to the present invention can be influenced. Low molecular weight polymers, or oligomers, will result a viscous composite material, whereby the use of oligomers comprising a relatively low number of monomers will result in an injectable semifluid and oligomers comprising a relatively high number of monomers will result in a material with putty-like properties.

The injectable semi-fluid and the putty-like composites according to the present invention are especially suitable as filler materials for bone fractures or defects with a bone regenerating capacity.

According to a particularly preferred embodiment of the present method in case low molecular weight polymers, or oligomers, are used, a crosslinking agent comprising at least one double or triple bond and a crosslinking radical initiator are added after step (a) but before step (c) and step (c) is crosslinking using photopolymerization, thermal polymerization or redox polymerization thereby providing an injectable or putty of said composite with bone forming properties.

The present copolymers of 1,3-trimethylene carbonate (TMC) according to the present invention are preferably chosen from the group consisting of 1,3-trimethylene carbonate (TMC) polymers with lactones cyclic esters, cyclic carbonates, cyclic ethers, cyclic anhydrides, and cyclic depsipeptides morpholine 2,5-dione derivatives. All these copolymers provide biodegradable composites according to the present invention.

According to a particularly preferred embodiment, the present copolymers of 1,3-trimethylene carbonate (TMC) according to the present invention are chosen from the group consisting of 1,3-trimethylene carbonate (TMC) polymers with polyethylene oxide (PEO), polyethylene glycol (PEG) and ε-caprolactone (CL), more preferably copolymers of 1,3-trimethylene carbonate (TMC) chosen from the group consisting of 1,3-trimethylene carbonate (TMC) polymers with 5-valerolacton, 1,5-dioxepane-2-one, and ε-caprolactone.

The present cross-linking agent if used in the methods according to the present invention is preferably chosen from the group consisting of acrylate-functionalized poly(trimethylenecarbonate)-based oligomer, an methacrylate-functionalized poly(trimethylenecarbonate)-based oligomer, a fumarate-functionalized poly(trimethylenecarbonate)-based oligomer, an acrylate-functionalized poly(D,L-lactide)-based oligomer, methacrylate-functionalized poly(D,L-lactide)-based oligomer, a fumarate-functionalized poly(D,L-lactide)-based oligomer, an acrylate-functionalized poly(L-lactide)-based oligomer, a methacrylate-functionalized poly(L-lactide)-based oligomer, a fumarate-functionalized poly(L-lactide)-based oligomer, an acrylate-functionalized poly(ε-caprolactone)-based oligomer, a methacrylate functionalized poly(ε-caprolactone)-based oligomer, a fumarate-functionalized poly(ε-caprolactone)-based oligomer, an acrylate-functionalized poly(ethylene glycol)-based oligomer, a methacrylate-functionalized poly(ethylene glycol)-based oligomer, a fumarate-functionalized poly(ethylene glycol)-based oligomer.

If present, the cross-linking agent of the present invention comprises 0.1% wt to 10% wt, preferably 0.5% wt to 8% wt, more preferably 1% wt to 5% wt of the cross-linking agent by weight percentage of the total weight of the present liquid polymeric composition.

The present methods as described above provide bone grafts, or composites, with advantageous bone forming or promoting, such as osteogenic and/or osteoinductive, properties not only resulting in bone formation but also in attachment of the generated bone to the surrounding bone structures.

Accordingly, according to a second aspect, the present invention relates to composites with bone forming, such as osteogenic and/or osteoinductive, properties obtainable by methods as described above.

As indicated, laminating the present composite on polymeric layers composed of acidic polymers and/or polymers providing acidic degradation products into a multilayered structure is not part of any method step according to the present invention and, accordingly, such laminates are not obtainable by the present methods.

The present bone forming or promoting, such as osteogenic and/or osteoinductive, agents embedded in the polymeric matrices according to the present invention provide not only bone formation but also attachment to, or connection with, the surrounding bone structures.

Accordingly, according to a third aspect, the present invention relates to composites with bone forming, such as osteogenic and/or osteoinductive, properties consisting of one or more agents with bone formation promoting, such as osteogenic and/or osteoinductive, properties as defined above embedded in a polymeric matrix of crosslinked homopolymers or copolymers of 1,3-trimethylene carbonate (TMC) as defined above.

As indicated above, depending on the molecular weight of the starting liquid or liquefied polymer provided, the properties of the present composite can be influenced.

Accordingly, according to a preferred embodiment of the present second or third aspect, the present composites are a molded article, an injectable or a putty.

The advantageous properties of the present composites, or bone graft, are particularly evident when using the present composites in the reconstruction bone fractures, or bone defects.

Accordingly, according to a fourth aspect, the present invention relates to the use of the present composites for providing bone regenerating implants, and especially the use of the present composites for providing implants for orbital floor reconstruction.

The present invention will be further detailed in the example below demonstrating the advantageous properties of the present composites in preferred embodiments. In the example, reference is made figures wherein:

FIG. 3: shows light micrographs of orbital implantations after three (A-F) and nine (G-L) months. Figure A, D, G and J show reconstruction with PTMC sheet. Capsule formation is visible; there is no sign of bone formation. New bone formation is clearly visible and in close contact with the BCP particles after three months in the present composite sheet (B, E) and shows progressive after nine months (H, K). Besides bone formation, also resorption of PTMC and disintegration of BCP particles is demonstrated. The laminated composite sheet also showed bone formation around BCP particles after three months (C, F). After nine months limited amounts of bone formation were found (I, L). (D-F and J-L are 4× magnifications of respectively A-C and G-I; (●) PTMC, (*) maxillary sinus, (b) bone, (■) PDLLA polymer, (arrow) residual PTMC polymer particles, (ct) connective tissue and (▲) designates area where remnants of disintegrated BCP particles are demonstrated.)

FIG. 6: shows epifluorescent confocal micrographs of intramuscularly implanted amounts of BCP (A-B) and the present composite (C-D). E-F and G-H are images of orbital implantations of the present composite after, respectively three and nine months. A, C, E, and G are bright field images, B, D, F, and H are epifluorescent images. Calcein=green, Xylenol Orange=red and Oxytetracycline=blue. It can be seen that bone formation had started after three weeks around the intramuscularly implanted amounts BCP and intramuscularly implanted composites near the edges, where the polymeric PTMC matrix had resorbed. The orbital implantations showed similar results. Bone formation had started after three weeks (E-F) in the three month group. Figures G-H show the process of bone formation being still active at nine months.

EXAMPLE

Introduction

Materials and Methods
Materials

Polymerization grade 1,3-trimethylene carbonate (TMC) was obtained from Boehringer Ingelheim, Germany. Stannous octoate (SnOct$_2$ from Sigma, USA) was used as received. High molecular weight poly(D,L-lactide) (PDLLA, with a 50/50 molar ratio of L- to D-lactide) was obtained from Purac Biochem, the Netherlands, and used as received. Biphasic calcium phosphate ceramic, (20±5% TCP and 80±5% HA), which was sintered at 1150° C. and sieved to particle sizes 45-150 μm, was obtained from Xpand Biotechnology, the Netherlands. The used solvents were of technical grade and purchased from Biosolve, the Netherlands.

Preparation of Composites and Laminates

Poly(trimethylene carbonate) (PTMC) was prepared by ring opening polymerization of trimethylene carbonate at 130° C. for a period of 3 days. Stannous octoate was used as a catalyst at a concentration of $2\times10^{-4}$ mol per mol of monomer. Analysis of the synthesized polymer by proton nuclear magnetic resonance ($^1$H-NMR), gel permeation chromatography (GPC) and differential scanning calorimetry (DSC) according to standardized procedures indicated that high molecular weight polymer had been synthesized.

GPC measurements showed that Mw=414,000 and Mn=316,000 g/mol, while NMR indicated that the monomer conversion was more than 98%. The glass transition temperature of this amorphous polymer was approximately −17° C., as thermal analysis showed.

The PTMC polymer was purified by dissolving in chloroform and precipitation into an excess of ethanol. Similarly, composites of PTMC with BCP particles were prepared by dissolving PTMC in chloroform at a concentration of 5 g/100 ml, after which the BCP was added and uniformly dispersed in the solution. The dispersion was then precipitated into a five-fold excess of ethanol 100%. The composite was collected and dried under vacuum at room temperature until constant weight was reached. PTMC/BCP composites containing 50 wt % corresponding to 30 vol % of CP were prepared.

After drying, the purified PTMC and the composite precipitate were compression moulded into 1.5 mm thick sheets at 140° C. and a pressure of 3.0 MPa (31 kg/cm$^2$) using a Carver model 3851-0 laboratory press (Carver, USA). The poly(D,L-lactide) was also of high molecular weight, and had an Mw=234,000 g/mol and an Mn=178,000 g/mol. NMR indicated that the residual monomer content was less than 1%. The glassy polymer was also amorphous, and had a glass transition temperature of approximately 52° C. This polymer was compression moulded into 0.3 mm thick sheets at 140° C.

Laminates of the PTMC/BCP composites and PDLLA were prepared by compression moulding PDLLA sheets onto sheets of the composite material at 140° C. The composite layer was 1.2 mm thick, while the PDLLA layer was 0.3 mm thick.

The prepared sheets were then sealed under vacuum and exposed to 25 kGy gamma irradiation from a $^{60}$Co source (Isotron BV, Ede, The Netherlands) for crosslinking.

Experimental Design of the Animal Study

All procedures performed on the animals were done according to international standards on animal welfare as well as being compliant with the Animal Research Committee of the University Medical Center Groningen.

Ten full-grown female Dutch Texel sheep were operated on and (evenly) divided into two groups. The first group had a follow-up of three months, the second a follow-up of nine months. Critical size irregularly shaped circular defects, 2.5-3.0 cm$^2$ were created in both orbital floors and reconstructed with:
1) a PTMC sheet,
2) a composite (PTMC/BCP) sheet or
3) a laminated composite (PTMC/BCP-PDLLA) sheet. Regarding the latter, the PDLLA layer faced towards the maxillary sinus.

To demonstrate osteoinduction, samples (1.5 mm×10 mm Ø) of the mentioned PTMC, composite and laminated composite sheets as well as an amount of 1 ml of BCP particles were also implanted intramuscularly in the back of the sheep. An overview is provided in Table 1 below.

TABLE 1

Overview of implantations and implantation sites for the three and nine month group

| Implantation material | 3 months | 9 months |
|---|---|---|
| BCP | IM: n = 5 | IM: n = 5 |
| PTMC | OF: n = 3 | OF: n = 3 |
|  | IM: n = 3 | IM: n = 3 |
| Composite | OF: n = 4 | OF: n = 4 |
| (PTMC/BCP) | IM: n = 4 | IM: n = 4 |
| Laminated composite | OF: n = 3 | OF: n = 3 |
| (PTMC/BCP-PDLLA) | IM: n = 3 | IM: n = 3 |

OF: orbital floor
IM: intramuscular

Furthermore, to assess the position of the reconstructed orbital floor, all sheep were evaluated by cone-beam computer tomography (CBCT) one week before and one week after surgery and at time of termination. To monitor the bone formation over time, fluorochrome markers were administered at nine, six and three weeks prior to the three and nine month termination. Bone formation was evaluated by histology and histomorphometry of non-decalcified sections using epifluorescent confocal and conventional light microscopy.

Surgical Procedure and Fluorochrome Labelling

Ten adult full-grown female Dutch Texel sheep, aged 24-36 months, were acquired and allowed to acclimatize for two weeks. The surgical procedures were performed under general anaesthesia. After the subciliar area was shaved and disinfected, both orbital floors were exposed using an infraorbital approach. The periosteum was elevated and the floor was fractured using a burr and/or chisel. Bone fragments were removed from the defect site. The bony defects created measured 2.5-3.0 cm$^2$ in size.

Then, the orbital floor was reconstructed using one of the implant materials (PTMC, composite or laminated composite sheet). Care was taken to ensure that the total defect was covered, for this the implant was tailored to size with a scissor. Implants were fixed with one titanium screw (1.5×3.5 mm, KLS-Martin, Germany) to prevent dislocation.

After reconstruction, the orbital periosteum was incised to mimic a traumatic situation (the incision allowed the orbital fat and musculature to prolapse into the orbit and exert force on the reconstruction material like in a real traumatic situation). The wound was closed in layers with resorbable sutures (Polyglactin 910, Ethicon, USA).

Simultaneously, intramuscular implantation of samples was performed in the paraspinal muscles. The muscle fascia was closed with non-resorbable sutures to mark the different implantation sites in the back (Polypropylene, Ethicon, USA). The other layers with resorbable sutures.

Prior to surgery amoxicilline was administered and continued for six days postoperative. Buprenorphin was administered for peri- and postoperative pain relief.

Fluorochrome markers were administered prior to termination. Calcein Green (10 mg/kg intravenously, Sigma, The Netherlands) was administered at nine weeks, Xylenol Orange (100 mg/kg intravenously, Sigma, The Netherlands) at six weeks and Oxytetracyclin (Engemycine 32 mg/kg intramuscularly, Mycofarm, The Netherlands) at three weeks prior to termination. After three and nine months follow-up, the animals were sacrificed by an overdose of pentobarbital (Organon, The Netherlands) and the implantation areas retrieved and fixed in a 4% phosphate-buffered formalin solution.

Histological Preparation

Fixed samples were rinsed with phosphate buffer solution (PBS), dehydrated in a series of ethanol solutions (70%, 80%, 90%, 96%, 100%×2) and embedded in methyl methacrylate (LTI, The Netherlands). Using a diamond saw (Leica SP1600, Leica Microsystems, Germany), histological sections (10-20 µm thick) were made along the plane perpendicular to the orbital floor for the former and parallel to the long axis of the implants for the latter. Sections for light microscope (Nikon Eclipse E200, Japan) observation were stained with 1% methylene blue (Sigma-Aldrich) and 0.3% basic fuchsin (Sigma-Aldrich) solutions, while unstained sections were made for epifluorescent confocal microscopy (Leica TCS SP2, Leica, Germany) observation.

Epifluorescent data was collected with 20× oil immersion objective, including transmitted light detection. The peak absorption (abs.) and emission (em.) wavelengths where: 351/364 nm abs. and 560 nm em., 543 nm abs. and 580 nm em., 488 nm abs. and 517 nm em., for respectively Tetracycline, Xylenol Orange and Calcein.

Histomorphometry and Statistics

Images of the stained sections for histomorphometric analysis were made using a slide scanner (Dimage Scan Elite 5400 II, Konica Minolta Photo Imaging Inc, Japan).

Histomorphometry was performed using Adobe Photoshop Elements 4.0 software. Briefly, the implant area was selected as the region of interest (ROI) and the corresponding number of pixels registered. Then both BCP particles and mineralized bone were pseudo-colored and the resulting numbers of pixels used to calculate the percentage of bone formation in the available space (available space is defined as the space between the BCP particles where the polymer has resorbed) as:

$$\text{Bone formation \%} = \frac{Bone pixels}{ROI - BCP pixels} \times 100\%$$

Averages and standard deviations were calculated for the percentage of bone formation in the available area. A Fisher's Exact Test was used to evaluate the differences in bone formation between the different materials as well as between the individual materials compared for the three and nine month group. The data sets were statistically evaluated using SPSS 17 (Statistical Package for the Social Sciences, SPSS Inc., USA). The null hypothesis (the means of each set are equal) was evaluated with 95% confidence level ($\alpha$=0.05).

Radiologic Examination

Cone-beam computed tomography (CBCT) scanning was performed to assess the position of the preoperative and postoperative (reconstructed) orbital floors, as well as at time of termination. CBCT scanning was carried out under general anaesthesia with propofol, The CBCT images were acquired with I-CAT Scanner with a 0.3 mm voxel size and a 170 mm field of view and stored for further analysis. Each scan was performed with the head of the animal in the same, reproducible position using the laser guide of the scanner as a reference.

Using Mimics Software (Materialise Dental, Belgium) three-dimensional (3D) reconstructions of all individual scans were made employing the same optimal threshold to depict the bone on each dataset.

Next the preoperative (intact) orbital floors and postoperative reconstructed orbital floors (i.e. the orbital floor implants) as well as the reconstructed orbital floors at time of termination were selected as region of interest (ROI).

Using Geomagic Studio Software (Geomagic Gmbh, Stuttgart, Germany) the 3D reconstructed scans were aligned and registered with the preoperative 3D reconstructed scans using an iterative closest point registration algorithm. The preoperative scan thus served as reference. Preoperative and postoperative (or at time of termination) orbital floors were highlighted.

Figure 6:
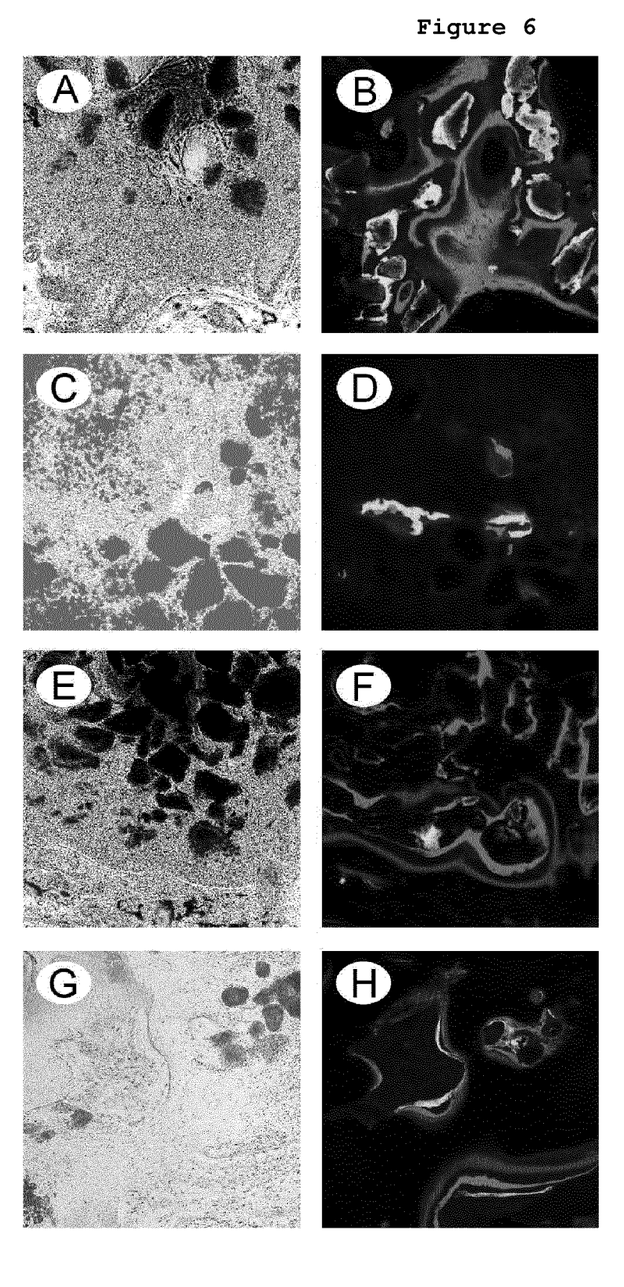

The deviation between the datasets was measured on a sliding colour scale which displayed the distances between the surfaces of the orbital floors (FIG. 6).

The mean negative deviation (i.e. at the level of the defect) for each implant was noted Table 2 below.

TABLE 2 deformations of the reconstructed orbital floors are provided for the different materials after 3 and 9 months postoperative. The animal that died after 6 months is evaluated separately. The preoperative scan served as reference. Subsequent the calculated maximum increase in volume of the orbit of the sheep after three and nine months for the different reconstruction materials are provided. For this the most negative deformation of each reconstruction material was used. The (maximum) increase in orbital volume occurred due to deformation of the reconstruction materials. (The defect size was considered to be 3 cm².)

| | PTMC | | Composite | | | Laminated composite | | |
|---|---|---|---|---|---|---|---|---|
| | 3 months | 9 months | 3 months | 6 months | 9 months | 3 months | 6 months | 9 months |
| | −0.8 mm | | | | −0.7 mm | | | −1.0 mm |
| | | −1.3 mm | −0.6 mm | | | | −0.7 mm | |
| | | −0.8 mm | | | −0.9 mm | −1.0 mm | | |
| | −1.0 mm | | | −1.1 mm | | −0.5 mm | | |
| | −0.5 mm | | | | −0.4 mm | −0.9 mm | | |
| | | −1.5 mm | 0.6 mm | | | | | |
| | | | −0.6 mm | | | | | −0.4 mm |
| | | | −1.3 mm | | | | | |
| Mean ± SD (mm) | −0.77 ± 0.25 | −1.20 ± 0.36 | −0.48 ± 0.79 | −1.1 | −0.67 ± 0.25 | −0.80 ± 0.26 | −0.7 | −0.70 ± 0.42 |
| Volume increase (cm³) | 0.16 | 0.23 | 0.19 | 0.16 | 0.14 | 0.15 | 0.11 | 0.15 |

In this way the deformation for the different reconstruction materials at the different time periods was determined. Next, the (overall) mean negative deformation for the different implants was calculated and used to establish the orbital volume increase, using the equation:

$$V_{increase} = \frac{1}{6}\pi h(3r^2 + h^2)$$

wherein:

$V_{increase}$=volume increase of the orbital cavity due to deformation of the reconstruction material (m³)

h=deformation of the disk-shaped implant (m)

r=0.0098 (m); this is the radius of a circular orbital floor defect measuring 3.0 cm²

Changes in orbital volume were used to assess the suitability of the different implants for reconstruction of orbital floor defects in sheep. An increase in orbital volume of +0.7 cm³ was considered the maximum allowable volume increase. Increases with volumes>0.7 cm³ can lead to enophthalmos and should therefore be avoided.

Results

During the in vivo experiment, none of the sheep showed signs of infection or adverse tissue reactions. Nine sheep remained in good health, one (otherwise healthy) animal died unexpectedly six months postoperatively. A performed autopsy did not reveal an obvious cause of death. No animals were excluded from this study. The prematurely deceased animal was evaluated as a separate 6 month time point group.

Descriptive Microscopic Observations of Intramuscular Implantations

After three and nine months all intramuscular implants were traced and the implantation sites harvested. Table 3 below provides an overview of the bone incidence for the different implants.

TABLE 3

Bone incidence in implantations after 3, 6 and 9 months and their consecutive percentages of bone formation in the available area as determined by histomorphometry. Mean ± standard deviation is presented

| Implanted material | Bone incidence 3 months | % bone | Bone incidence 6 months | % bone | Bone incidence 9 months | % bone |
|---|---|---|---|---|---|---|
| BCP particles | IM: 2/5 | 2.9 ± 5.9 | IM: 1/1 | 12.8 | IM: 2/4 | 6.4 ± 6.9 |
| PTMC | OF: 0/3 | 0 ± 0 | NI | | OF: 0/3 | 0 ± 0 |
| | IM: 0/3 | 0 ± 0 | NI | | IM: 0/3 | 0 |
| Composite | OF: 3/4 | 7.7 ± 8.1 | OF: 1/1 | 14.9 | OF: 3/3 | 15.7 ± 14.6 |
| | IM: 2/4 | 0.3 ± 0.6 | IM: 0/1 | 0 | IM: 0/3 | 0 |
| Laminated composite | OF: 3/3 | 5.3 ± 4.0 | OF: 1/1 | 13.9 | OF: 1/2 | 1.7 ± 2.4 |
| | IM: 2/3 | 2.0 ± 1.9 | IM: 0/1 | 0 | IM: 0/2 | 0 |

OF: orbital floor
IM: intramuscular
NI: not implanted

Light microscopical evaluation of the stained sections showed that bone formation was present in most of the implantations that contained BCP particles. Implantations of PTMC alone (i.e. not a composite with BCP) did not lead to formation of bone in any of the sheep.

Figure 1:
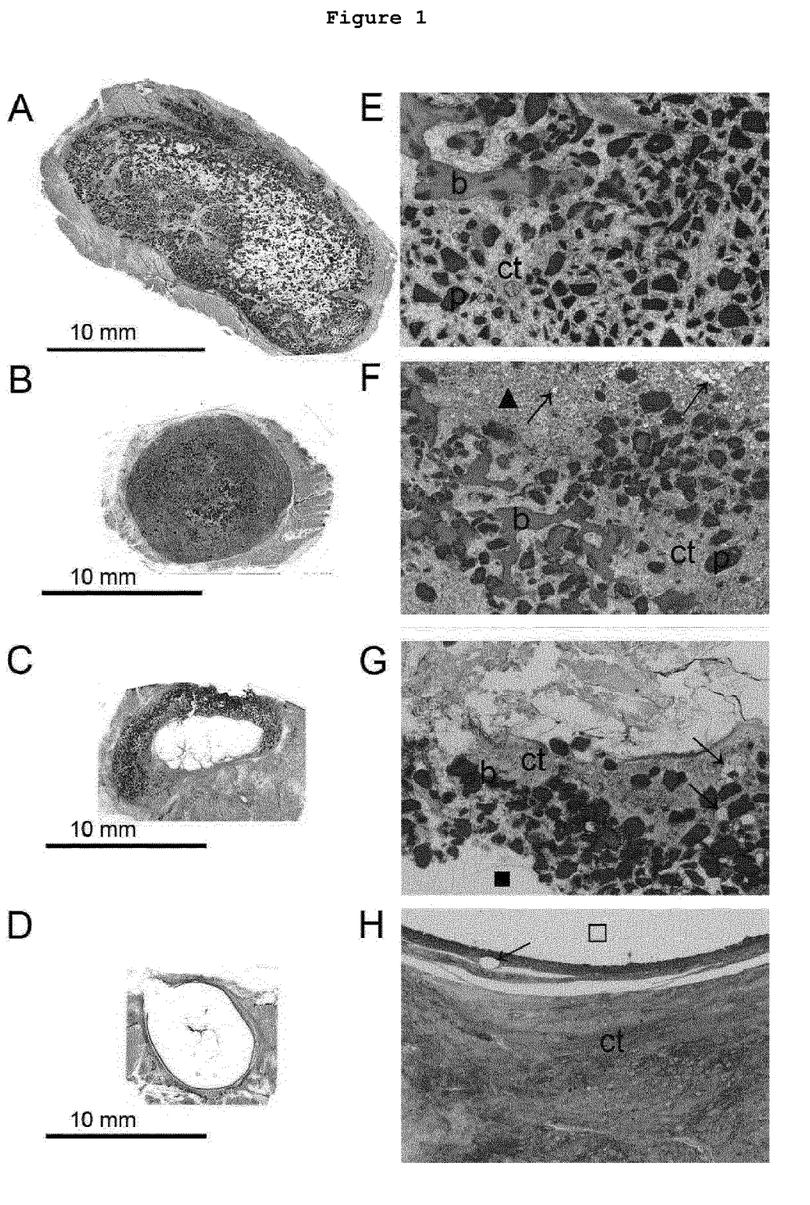
FIG. 1: shows light micrographs of intramuscular implantation sites after three months. Figures A-D represent overviews of intramuscular implantations of respectively BCP, the present composite, laminated composite and PTMC. Figures E-H represent magnifications (4×) of the overviews. Bone (b) is clearly visible and in close contact with the BCP particles (p) in figures A-C and their corresponding magnifications. The PTMC (●) matrix has resorbed extensively, phagocytosed polymer particles (arrows) can be observed. (▲) designates an area where remnants of disintegrated BCP particles are demonstrated. (■) PDLLA polymer.

FIG. 1 provides an overview of the intramuscular implantations after three months. Light microscopical observations showed that, when present, bone had formed around the BCP particles and was in close contact with the surface of the particles. Besides bone formation, connective tissue ingrowth was observed. Furthermore it was shown that for the implanted composites the PTMC polymer matrix had resorbed profoundly. Only small amounts of PTMC were found. The PDLLA layer of the laminated composite could still be identified. The PTMC implantations did not show any bone formation. The PTMC polymer could still be identified and was surrounded by a fibrous capsule of dense connective tissue.

Figure 2:
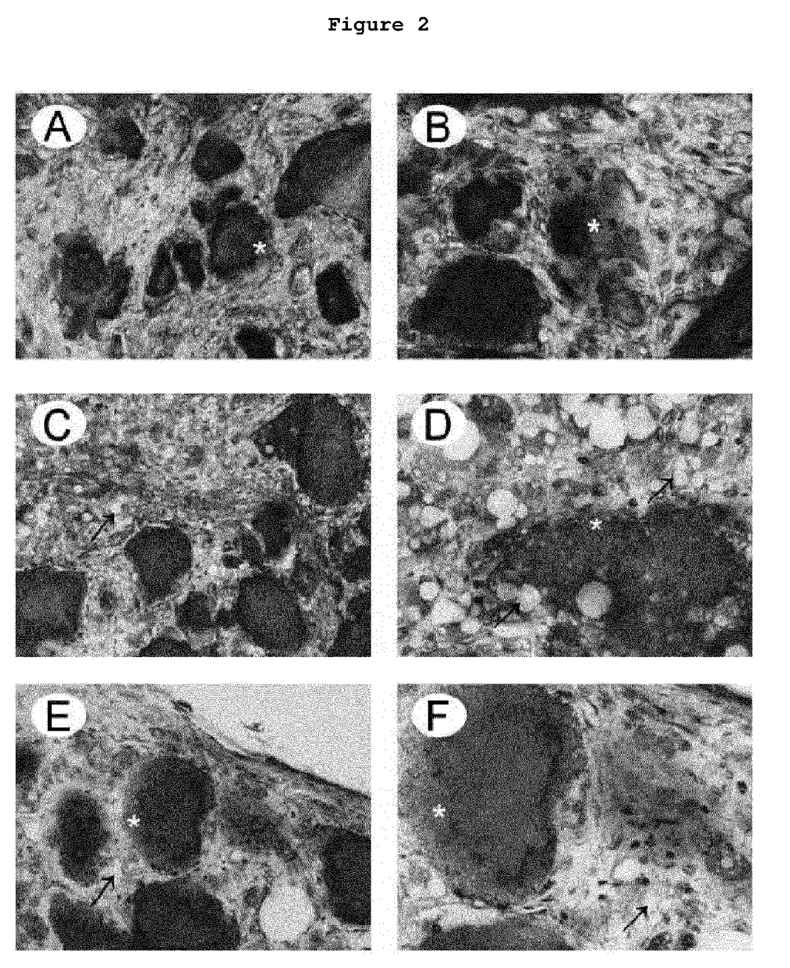
FIG. 2: shows light micrographs (20×-40×) of intramuscular implantations after three months of respectively pure BCP particles (A, B), the present composite (C, D) and laminated composite (E, F). BCP particles are surrounded by phagocytic cells. The dust-like aspect at the surface of the particles suggests disintegration. Remaining PTMC particles (arrows) are easily identified. (A, C and E are 20× magnifications, B, D and F 40×)

Besides signs of the degradation of the polymers, also disintegration of the BCP particles was observed. In FIG. 2, the degradation of the PTMC polymeric matrix and the disintegration of the BCP particles is shown at higher magnifications. Closer observations showed that recruitment of phagocytic and multi-nucleated giant cells had occurred. These cells surrounded and adhered to the remnants of the PTMC polymeric matrix as well as to the surface of the BCP particles.

After nine months the implantations of pure BCP particles showed progressive bone formation, while none of the intramuscular implanted (laminated) composites showed bone formation. The polymeric PTMC matrix of the composite had resorbed almost completely, only few phagocytosed PTMC particles were observed. Signs of disintegration of the BCP particles were also observed after nine months in all implantations containing BCP particles.

The intramuscularly implanted samples of PTMC were still identified, although signs of degradation were progressive. Implants were still surrounded by a fibrous capsule consisting of dense connective tissue.

Descriptive Microscopic Observations of Orbital Implantations

Figure 3:
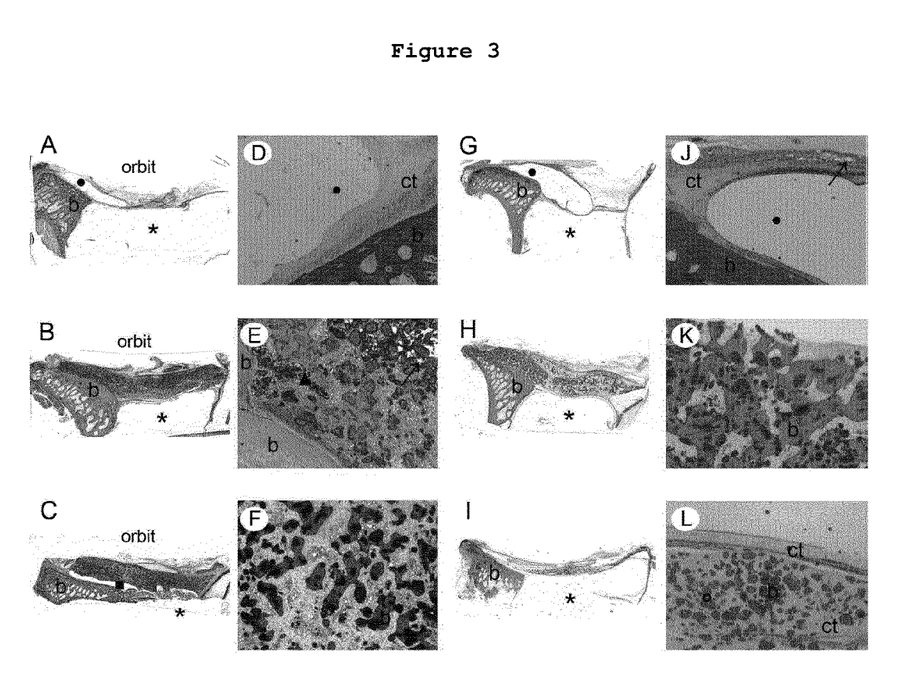
Figure 4:
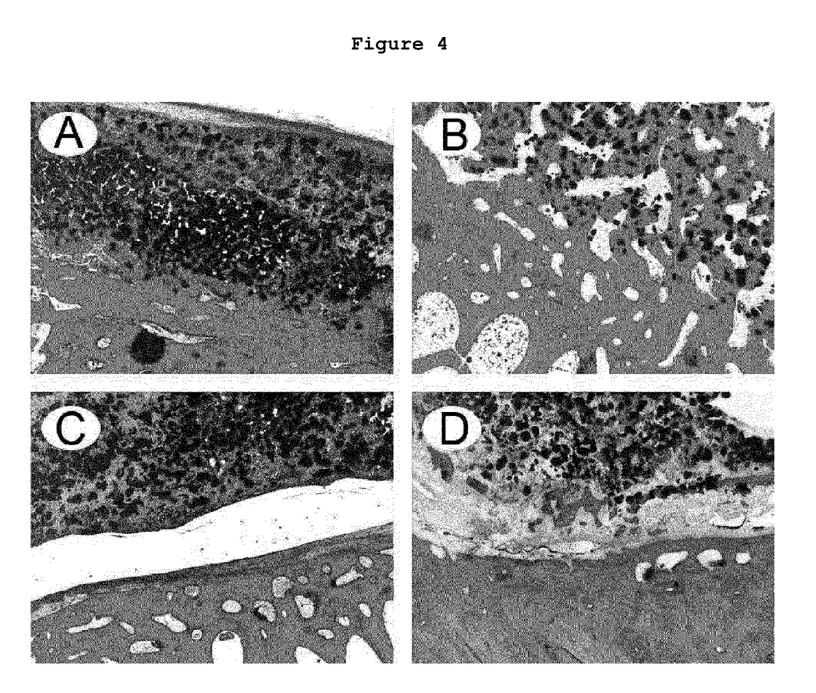
FIG. 4: shows light micrographs (2.5×) representing the transition area of the present composite (A, B) and laminated composite (C, D) implant (and newly formed bone) to host bone in the orbit of the sheep. Figures A and B show excellent osseous integration of newly formed bone with the host bone after respectively 3 and 9 months. Figure C clearly illustrates the PDLLA layer of the laminated composite impeding osseous integration after three months. Figure D shows that after 9 months, although the PDLLA layer has degraded, osseous integration of newly formed bone with the host bone still has not occurred. This could be due to the fibrous capsule which is present between the newly formed bone and host bone.

The results for the orbital implantations are shown in Table 3 and FIG. 3. After three months, the composite and laminated composite implants clearly showed bone formation. Most of the polymeric PTMC matrix had resorbed, only small remnants of PTMC were observed. The newly formed bone was in close contact with the BCP particles. Moreover, the newly formed bone in the composite implants showed osseous integration with the host bone at places (i.e. the bone of the animal) where the composite implants were in contact with the host bone (i.e. at the orbital floor defect borders) (FIG. 4).

At the level of the defect, where the composite implants were consequently not in contact with the host bone, several layers of dense connective tissue covered the implants. The laminated composites, by contrast, did not show this osseous integration of newly formed bone with host bone and were completely surrounded by a fibrous capsule composed of dense connective tissue (FIG. 4).

After nine months the bone formation appeared to be progressive for the composite implants. Both the composite implants and laminated composite implants showed almost complete resorption of the polymeric PTMC matrix. Only phagocytised PTMC polymer was observed. The PDLLA layer seemed to have been resorbed completely at this time point. Whereas the newly formed bone in the composite implants still showed integration with the host bone, the laminated composites were still surrounded by the fibrous capsule and subsequently did not.

Figure 5:
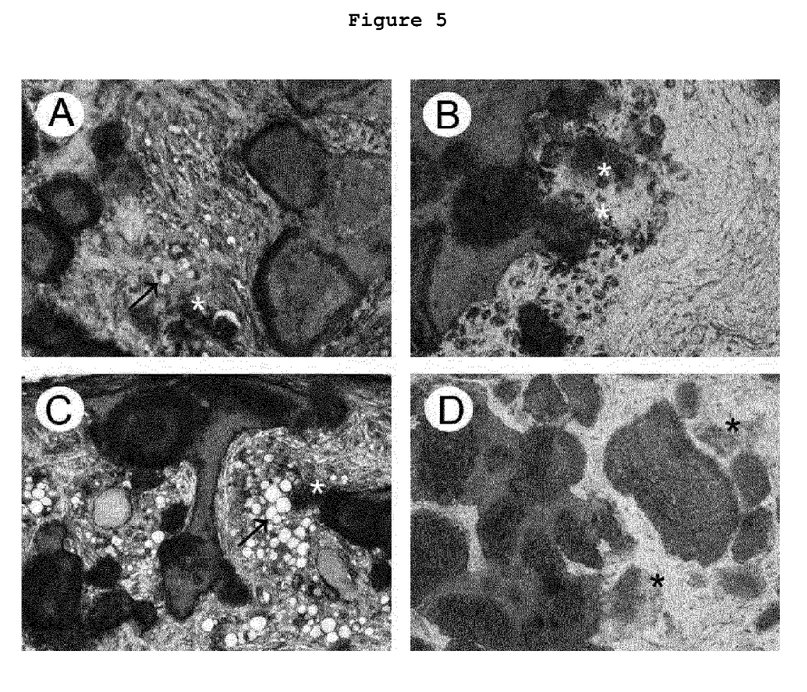
FIG. 5: shows light micrographs (20×) showing the disintegration of BCP particles in the orbital implantations after three and nine months. Figure A-B represent the present composite implants, C-D represent laminated composite implants. BCP particles are surrounded by phagocytic cells. The 'dusty' aspect of the particles suggests disintegration. Residual PTMC particles (arrows) are easily identified. The disintegration of the BCP particles in the composite and laminated composite tended to be more extensive compared to the disintegration in the intramuscular implantations containing BCP particles only. (*) shows area where BCP is disintegrating, (arrow) phagocytosed PTMC.

Signs of disintegration of the BCP particles were also found in the orbital implants. FIG. 5 shows a composite implant and laminated composite implant after three and nine months at higher magnifications. Recruitment of phagocytic cells was also observed here. These cells adhered to the BCP particles as well as to remnants of the PTMC.

The histological findings for the animal that died after six months were comparable to the observations found for the other animals after nine months. In this animal the orbital composite implant showed new bone formation that had integrated with the host bone. Although the laminated composite implant placed in the other orbit did show bone formation, the newly formed bone (again) had not integrated with the host bone. A fibrous capsule surrounded the laminated composite implant. Besides the implanted amounts of pure BCP particles, none of the intramuscular implantations demonstrated bone formation (Table 3).

The degradation and resorption of the polymer matrix and PDLLA layer showed to be progressive compared to the specimens after three months, but was not as advanced as in the nine month group. Remnants of the PDLLA layer were still identified. Disintegration of the BCP particles was also observed in all implantations containing BCP particles.

Fluorescence Microscopy

Epifluorescent confocal microscopy of the sequential fluorochrome labels revealed that upon three weeks after implantation formation of bone had started in the intramuscular implantations of pure BCP particles and (laminated) composites. Similar observations were found for the composite and laminated composite implantations in the orbital implantations (FIG. 6).

Analysis of the fluorochrome labels indicated that the bone formation started at the surface of the BCP particles and progressed toward the periphery. After nine months the fluorochrome labelling showed that the process of bone formation and remodelling was still active in the orbital floor implants. None of the intramuscular implanted (laminated) composite samples showed fluorescent labelling after nine months.

Histomorphometry

The results of the histomorphometrical analysis for the intramuscular and orbital implantations are shown in Table 3. The mean percentages and standard deviations are presented for the bone formation in the available area: defined as the space between the BCP particles where the polymer has resorbed. Besides the fact that not all animals showed bone formation in every implantation, large variations in the amounts of formed bone (when present) in and between the individual animals were found.

After three months measurements showed 7.7±8.1% (mean±SD) of bone had formed in the composite orbital floor implantations. After nine months the percentage of bone had increased to 15.5±12.0%. The laminated composite orbital floor implants showed 5.3±4.0% and 1.7±2.4% of bone formation, respectively after three and nine months. The intramuscular implantations showed limited bone formation.

The intramuscularly placed composite samples demonstrated 0.3±0.6% and the laminated composite 2.0±1.9% of bone formed after three months. The intramuscularly placed amounts of pure BCP particles showed 2.9±5.9% bone formation, which progressed to 6.4±6.9% of bone, after nine months.

The prematurely deceased animal showed respectively 13.9% and 14.9% of bone formation for the laminated composite and composite implantations in the orbits. The intramuscular implanted pure BCP particles measured 12.8% of bone formation.

Evaluation by CBCT

Figure 7:
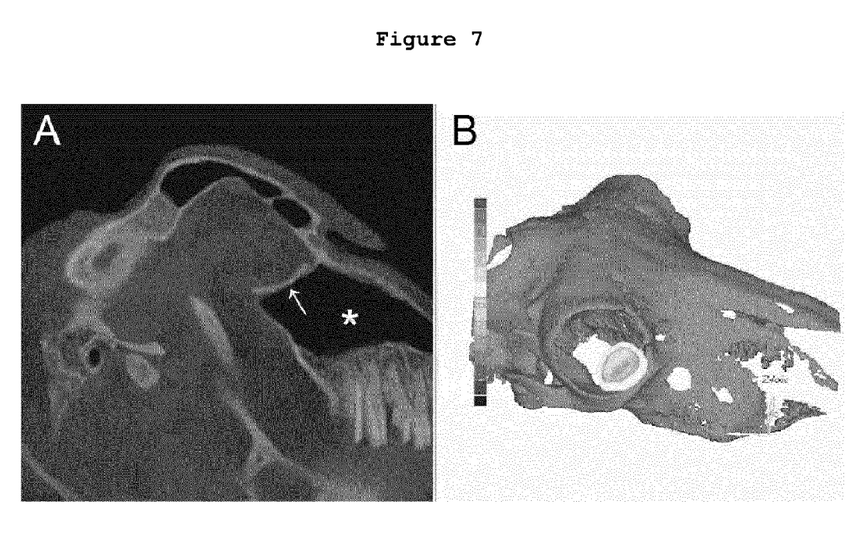
FIG. 7: shows assessment of orbital floor position. Figure A shows a lateral view of a postoperative CBCT scan of a sheep. The present composite implant (arrow) has radio-opaque properties and can be clearly identified at the top of the maxillary sinus (*). Figure B shows the superposition of the postoperative scan over the preoperative scan. The region of interest is highlighted. There is a slight 'negative' deformation at the center of the implant when compared to the preoperative situation. Where the implant overlies the defect borders (i.e. is resting on the intact orbital floor borders), the deformation is slightly 'positive' when compared to the preoperative situation of the intact orbital floor.

FIG. 7 graphically presents the evaluation process of the reconstruction of the orbital floors and illustrates the performance of the implants. It can be seen that the radio-opaque composite and laminated composite sheets were easily identified. As stated, the colour mapping shows the changes in deviation of the reconstructed orbital floor compared to the preoperative intact orbital floor.

The results for the deformation and maximum calculated changes in orbital volume due to deformation of the implants for the different time periods are summarized in Table 2.

It can be seen that the increase of the orbital volume in animals treated with the PTMC implants ranged from +0.16 to +0.23 $cm^3$, respectively after three and nine months. The animals treated with the composite implants showed an orbital volume increase ranging from +0.14 to +0.19 $cm^3$, while the animals treated with the laminated composite implants showed volume increases ranging from +0.11 to +0.15

Discussion

The present example describes the evaluation of the osteoinductive properties of composite materials composed of PTMC and microstructured BCP. The composite materials were evaluated both in an orthotopic (orbit) as well as in an ectopic (intramuscular) site in sheep. Simultaneously with the evaluation of the osteoinductive properties of the composite materials, the suitability of the composite materials to serve as a load bearing material was assessed.

It was shown that the PTMC/BCP composite materials and the PDLLA-laminated PTMC/BCP composite materials have osteoinductive properties. Moreover, fluorochrome labelling indicated that the osteoinductive potential of the composites remained active at nine months.

During the surgical procedures, it became clear that regarding the shape-ability the composite and the laminated composite, as well as the PTMC implants could be cut easily into the desired shape. Most importantly, the present results showed that the composite as well as the laminated composite implants exerted osteoinductive properties. Moreover, the composite implants, in contrast with the laminates, showed excellent osseous integration of the newly formed bone with the host bone.

The histological observations of the degradation of the polymeric PTMC matrix with simultaneous formation of bone supported the hypothesis that a resorbable polymeric matrix could enhance the mechanical properties of calcium phosphate ceramics, without negatively affecting the osteoinductive properties of the calcium phosphate particles.

For the laminated composites, however, a negative effect on bone formation as well as osseous integration of newly formed bone with host bone was observed.

The present composites, besides not showing hindrance to regeneration of normal/local tissue (excellent osseous integration), can also be expected to have a more favourable surface-to-volume ratio, since the degradation process can continue along the exposed BCP particles, thereby increasing the surface-to-volume ratio.

The relatively large variations of induced amounts of bone that that were observed in and between the individual animals are not uncommon with research concerning osteoinductive materials. It is known that besides animal-specific factors have an effect on the amount of induced bone, implantation site-specific factors also play a role.

Orthotopic locations tend to give larger amounts of induced bone compared to ectopic locations. Also, it is suggested that the intrinsic ability of individual animals to form new bone in osteopromotive environments could vary because of genetic factors leading to different responses to exogenous cells (e.g. exogenous bone morphogenetic proteins (BMPs) as well as different actions of endogenous cells involved in the process of osteoinduction.

The evaluation by CBCT showed that all the reconstructed orbital floors were adequately positioned compared to the preoperative anatomical situation. None of the calculated volume increases, due to deformation of the implants, of the orbits were above the aforementioned critical value of 0.7 cm$^3$ (Table 2).

CONCLUSIONS

The present example describes the preparation and evaluation of osteoinductive composites composed of PTMC and microstructured BCP particles. From the results it can be concluded that the composite materials are shapeable, exert osteoinductive and osteogenic properties and show integration with, or attachment to, the surrounding host bone.

The invention claimed is:

1. A method for providing a composite with bone forming properties, said method comprising the steps of:
    a) providing a liquid, or liquefied, polymeric composition comprising:
        homopolymers of 1,3-trimethylene carbonate (TMC) with a Mw of more than 250,000 g/mol; or
        copolymers of TMC with a Mw of more than 250,000 g/mol, wherein said copolymer of TMC is chosen from the group consisting of TMC polymers with polyethylene oxide (PEO), polyethylene glycol (PEG) and e-caprolactone (CL);
    b) adding to said liquid, or liquefied, polymeric composition one or more agents with bone forming properties thereby providing a dispersion of said agents in said liquid or liquefied polymeric composition, wherein said one or more agents with bone forming properties are one or more compounds selected from the group consisting of calcium phosphates, hydroxyapatite, tricalcium phosphate, Bioglass, calcium sulphate, octacalcium phosphate, and biphasic calcium phosphate and combinations thereof; and
    c) crosslinking the dispersion, or a solidified form thereof to obtain a composite with bone forming properties.

2. The method according to claim 1, wherein the dispersion of said agents in the liquid or liquefied polymeric composition of step (b) comprises 5 wt % to 95 wt % of said one or more agents with respect to the total weight of the polymer in the dispersion.

3. The method according to claim 1, wherein said homopolymers or copolymers are liquefied by dissolution in a solvent.

4. The method according to claim 1, comprising, after step (b) but before step (c), a step comprising solidifying said dispersion and subsequently moulding said solidified dispersion into a desired shape.

5. The method according to claim 1, wherein step (c) is crosslinking said dispersion, or solidified form thereof, using gamma radiation with an irradiation dose of 10 to 100 kGy thereby providing an elastomeric composite with bone forming properties.

6. The method according claim 3, wherein said solvent is selected from the group consisting of acetone, dichloromethane, chloroform, carbontetrachloride, ethylene carbonate, propylene carbonate, dimethylsulfoxide, toluene, benzene, tetrahydrofuran and 1,4-dioxane.

7. The method according to claim 2, wherein the dispersion of said agents in the liquid or liquefied polymeric composition of step (b) comprises 30 wt % to 70 wt % of said one or more agents with respect to the total weight of the polymer in the dispersion.

8. The method according to claim 4, wherein said solidifying comprises solidifying by precipitation, or solidifying at a temperature below the glass transition temperature of the homopolymers or copolymers of TMC.

9. A method for providing a composite with bone forming properties, said method comprising the steps of:
    a) providing a liquid, or liquefied, polymeric composition comprising:
        homopolymers of 1,3-trimethylene carbonate (TMC) with a Mw of more than 250,000 g/mol; or
        copolymers of 1,3-trimethylene carbonate (TMC) with a Mw of more than 250,000 g/mol;
    b) adding to said liquid, or liquefied, polymeric composition one or more agents with bone forming properties thereby providing a dispersion of said agents in said liquid or liquefied polymeric composition, wherein said one or more agents with bone forming properties are one or more compounds selected from the group consisting of calcium phosphates, hydroxyapatite, tricalcium phosphate, Bioglass, calcium sulphate, octacalcium phosphate, and biphasic calcium phosphate and combinations thereof;
c) solidifying said dispersion and subsequently moulding said solidified dispersion into a desired shape; and
d) crosslinking said solidified dispersion using gamma radiation with an irradiation dose of 10 to 100 kGy thereby providing an elastomeric composite with bone forming properties.

10. The method according to claim 9, wherein the dispersion of said agents in the liquid or liquefied polymeric composition of step (b) comprises 5 wt % to 95 wt % of said one or more agents with respect to the total weight of the polymer in the dispersion.

11. The method according to claim 10, wherein the dispersion of said agents in the liquid or liquefied polymeric composition of step (b) comprises 30 wt % to 70 wt % of said one or more agents with respect to the total weight of the polymer in the dispersion.

12. The method according to claim 9, wherein said homopolymers or copolymers are liquefied by dissolution in a solvent.

13. The method according to claim 9, wherein said copolymer of TMC is chosen from the group consisting of TMC polymers with lactones cyclic esters, cyclic carbonates, cyclic ethers, cyclic anhydrides, and cyclic depsipeptides morpholine 2,5-dione derivatives.

14. The method according to claim 9, wherein said copolymer of TMC is chosen from the group consisting of TMC polymers with polyethylene oxide (PEO), polyethylene glycol (PEG) and e-caprolactone.

15. The method according to claim 9, wherein said copolymer of TMC is chosen from the group consisting of TMC polymers with 5-valerolacton, 1, 5-dioxepane-2-one, and e-caprolactone.

16. The method according to claim 9, wherein said solidifying comprises solidifying by precipitation, or solidifying at a temperature below the glass transition temperature of the homopolymers or copolymers of TMC.

* * * * *

UNITED STATES PATENT AND TRADEMARK OFFICE
CERTIFICATE OF CORRECTION

PATENT NO. : 9,913,932 B2  
APPLICATION NO. : 14/353486  
DATED : March 13, 2018  
INVENTOR(S) : Dirk Wybe Grijpma Page 1 of 1

It is certified that error appears in the above-identified patent and that said Letters Patent is hereby corrected as shown below:

On the Title Page

Item (73) please correct the name of the second assignee so that it reads:
-- (73) Assignees: RIJKSUNIVERSITEIT GRONINGEN --.

Signed and Sealed this
Fifteenth Day of May, 2018

Andrei Iancu
*Director of the United States Patent and Trademark Office*